United States Patent
Skarping et al.

(10) Patent No.: US 10,634,586 B2
(45) Date of Patent: Apr. 28, 2020

(54) FLUID-TIGHTLY SEALABLE SAMPLING DEVICE

(71) Applicant: PROVTAGAREN AB, Hässleholm (SE)

(72) Inventors: Gunnar Skarping, Hässleholm (SE); Marianne Dalene, Hässleholm (SE)

(73) Assignee: PROVTAGAREN AB, Hässleholm (SE)

( * ) Notice: Subject to any disclaimer, the term of this patent is extended or adjusted under 35 U.S.C. 154(b) by 998 days.

(21) Appl. No.: 14/894,041

(22) PCT Filed: May 28, 2014

(86) PCT No.: PCT/SE2014/050659
§ 371 (c)(1),
(2) Date: Nov. 25, 2015

(87) PCT Pub. No.: WO2014/193302
PCT Pub. Date: Dec. 4, 2014

(65) Prior Publication Data
US 2016/0103043 A1 Apr. 14, 2016

(30) Foreign Application Priority Data
May 29, 2013 (SE) ...................................... 1350651

(51) Int. Cl.
*G01N 33/538* (2006.01)
*G01N 1/22* (2006.01)
(Continued)

(52) U.S. Cl.
CPC ............. *G01N 1/2214* (2013.01); *G01N 1/14* (2013.01); *G01N 1/20* (2013.01); *G01N 1/22* (2013.01);
(Continued)

(58) Field of Classification Search
CPC .......... G01N 1/2214; G01N 1/14; G01N 1/20; G01N 1/22; G01N 1/2205; G01N 1/2247; G01N 1/405; G01N 33/497; G01N 33/5375; G01N 33/538; G01N 33/5436; G01N 1/22015; G01N 2001/2223; G01N 2001/022; G01N 2001/007; G01N 2001/4088; B01L 2300/042
See application file for complete search history.

(56) References Cited

U.S. PATENT DOCUMENTS 3,954,428 A 5/1976 Marple et al.
4,367,081 A 1/1983 Harvey
(Continued)

FOREIGN PATENT DOCUMENTS

CN 1447913 A 10/2003
CN 1639555 C 7/2005
(Continued)

*Primary Examiner* — Gailene Gabel
(74) *Attorney, Agent, or Firm* — Preti Flaherty; Beliveau & Pachios LLP (57) ABSTRACT

A fluid-tightly sealable sampling device for analysis of one or more substances in a fluid flow intended to pass through the sampling device is disclosed, wherein it comprises an adsorption device (1) which is hollow and is adapted to be provided with one or more reagents for adsorption of and reaction with said one or more substances in the fluid flow, a filter holder (2), which is hollow and is connected in a fluid-tight way with the adsorption device (1), a filter device (4) adapted to be provided with one or more reagents for adsorption of and reaction with said one or more substances in the fluid flow, a gasket (5) provided with at least one projection (6) engaged with at least one corresponding receiving slot in the filter holder (2), a first external cap (9) detachably connected with the inlet end of the sampling device in a fluid-tight way and a second external cap (13) detachably connected with the outlet end of the sampling device in a fluid-tight way.

39 Claims, 5 Drawing Sheets

(51) Int. Cl.
*G01N 1/14* (2006.01)
*G01N 1/20* (2006.01)
*G01N 1/40* (2006.01)
*G01N 33/543* (2006.01)
*G01N 33/537* (2006.01)
*G01N 1/02* (2006.01)
*G01N 1/00* (2006.01)

(52) U.S. Cl.
CPC ......... *G01N 1/2205* (2013.01); *G01N 1/2247* (2013.01); *G01N 1/405* (2013.01); *G01N 33/538* (2013.01); *G01N 33/5375* (2013.01); *G01N 33/5436* (2013.01); *G01N 2001/007* (2013.01); *G01N 2001/022* (2013.01); *G01N 2001/2223* (2013.01); *G01N 2001/4088* (2013.01)

(56) References Cited

U.S. PATENT DOCUMENTS

| | | |
|---|---|---|
| 6,632,681 B1 | 10/2003 | Chu |
| 6,634,243 B1 | 10/2003 | Wickstead et al. |
| 7,098,040 B2 | 8/2006 | Kaylor et al. |
| 2002/0048819 A1* | 4/2002 | Alley ................ B01L 3/502 436/169 |
| 2005/0112024 A1 | 5/2005 | Guo et al. |
| 2006/0239857 A1 | 10/2006 | Skarping et al. |
| 2008/0260581 A1 | 10/2008 | Rosman et al. |
| 2009/0117663 A1 | 5/2009 | Skarping et al. |
| 2009/0242470 A1* | 10/2009 | Muenkel ............ B01D 35/30 210/148 |
| 2010/0012589 A1 | 1/2010 | Ribault et al. |
| 2010/0288691 A1 | 11/2010 | Shigesada et al. |
| 2010/0297691 A1 | 11/2010 | Ribeiro et al. |

FOREIGN PATENT DOCUMENTS

| | | |
|---|---|---|
| CN | 1898544 A | 1/2007 |
| CN | 1910438 B | 2/2007 |
| CN | 101893523 A | 11/2010 |
| CN | 101909757 B | 12/2010 |
| CN | 202119661 U | 1/2012 |
| GB | 2085158 A | 4/1982 |
| GB | 2266477 A | 11/1993 |
| WO | WO 00/75622 | 12/2000 |
| WO | 2009/067503 A1 | 5/2009 |
| WO | WO 2011/108981 | 9/2011 |
| WO | WO 2011/108981 A1 | 9/2011 |
| WO | WO 2013/036127 A1 | 3/2013 |

* cited by examiner

FLUID-TIGHTLY SEALABLE SAMPLING DEVICE

FIELD OF THE INVENTION

The present invention relates to a fluid-tightly sealable sampling device for environmental and medical analysis of one or more substances in a fluid flow intended to pass through the sampling device.

BACKGROUND ART

There is a clear demand for the monitoring of air-borne compounds that may have health effects on exposed individuals. A great interest exists for compounds that have occupational exposure limit values, set by governmental bodies, to ensure that the levels of such compounds are satisfactory low. In many cases it is not known what the air contaminants consist, of and for this reason it is of interest to learn more details about the nature of these "unknown" compounds and to reveal the identity of the most predominate ones. Another field of interest is to study and check the effect of measures with a view to reducing these levels in air, e.g. to check the "true" ventilation efficiency or other measures to control the air levels. Devices for this purpose can also be used for the monitoring of the quality of compressed air and air in respiratory protective devices. Other fields of application for such devices are e.g. the control of different volatile compounds present in food. Such compounds can be used as markers for degradation of certain food components or to monitor raw materials to ensure a satisfactory quality. Such devices may also be used to ensure that other compounds not have contaminated food. In hospitals such devices can be used to check the air levels of e.g. narcosis gases and to ensure that the personnel, patients and others are not exposed to toxic levels. Chemical warfare agents are also compounds that need to be checked for in order to reveal the presence thereof and to ensure that individuals are not exposed.

In environmental analysis there is a need to monitor the quality of air in cities, public places and in the nature. One purpose is to obtain background data for statistical studies and to check if the levels are below the levels set by national and international bodies. Such devices can also be used to check if the emission of industrial pollutants results in exposure in the nature or in populated areas. The achieved data can have an impact on decisions and interpretation of a certain situation. There is therefore a demand of a satisfactory high quality of the data.

There are many examples of air pollutants that occur in both gas and particle phase. Of special interest are the size fractions that have the ability to reach the lower respiratory tract. There are reasons to believe that the toxicology is different depending on not only the chemistry as such but also on the distribution on different target organs in the body of humans. There is a need to know more about the exposure to the respirable particle fraction present in air.

Numerous devices exist for the monitoring of air-borne compounds and there is a great variety of technology used. In principle, the devices can be grouped in selective and non-selective devices. Non-selective devices give a response for several compounds and do not differentiate between two or several compounds and may also result in false positive results. Such devices are today still used, possibly due to the low cost. In many applications, false positive results can give rise to a high cost for the user, if costly measures are performed from invalid data.

Selective devices give a certain response for a selected compound or a group of compounds. Other present compounds do not interfere with the result. The frequency of false positive results will be much less as compared to non-selective monitoring. The quality of the data obtained is essential. Typical factors that describe the quality of the data are: repeatability, reproducibility, linearity (calibration graph characteristics with intercept and background), detection limit and quantification limit. In addition, knowledge regarding the interference from other compounds is necessary. It needs to be mentioned that a certain compound can influence the result even if the compound does not itself give rise to a response.

Similar techniques for the detection of air-borne compounds involves the use of e.g. photo ionisation detectors (PID, Thermo Scientific, Franklin, Mass., USA), flame ionisation detectors (FID, Thermo Scientific, Franklin, Mass., USA), infrared detectors (IR), portable gas chromatography (GC)-PID (PID Analyzers, Pembroke Mass., USA), portable GC-mass spectrometers (MS, Inficon Inc., New York, USA), GC-DMS ((Differential Mobility Spectrometry), Sionex Inc., Bedford, Mass., USA). All techniques give a response for a certain analyte, but to know the concentration the response needs to be translated into concentration by using information from a more or less sophisticated calibration curve. For many of the above techniques, the response varies with time due to ageing, contamination of the detector (reduces the signal) and other variables.

The GC-DMS technique mentioned above is used in the MicroAnalyser instrument (Sionex Inc., Bedford, Mass., USA). The GC-DMS technique is based on GC separation, with regards to compound volatility, in combination with the separation in a DMS sensor, with regards to other molecular properties such as size shape, charge etc.

There are several drawbacks with the present types of instruments. For PID and FID, identification of the individual chemicals is not possible. PID and FID detectors measure the sum of VOC (Volatile Organic Compounds). Infrared detectors suffer from problems with inferences. IR detectors are not possible to use when monitoring VOCs at low concentration when other interfering compounds are present.

Polyurethane (PUR) products as air pollutants are of particular interest to monitor and analyze. They frequently occur in industry, in particular in manufacturing and handling polyurethane foam, elastomers, adhesives and lacquers. Polyurethane is produced by the reaction of a bifunctional isocyanate with a polyfunctional alcohol. The satisfactory technical qualities of polyurethane have resulted in a large increase of its use and application fields during the last decades. In connection with thermal decomposition of polyurethanes, however, the formation of isocyanates, aminoisocyanates, anhydrides, and amines might occur, and extremely high contents can be found in air, e.g. when welding automobile sheet steel. Besides the known types of isocyanate, also new types of aliphatic isocyanates have been detected, in connection with e.g. heat treatment of car paint. Most of the isocyanates formed have been found to be represented by so-called low-molecular isocyanates. During short periods of time (peak exposure) particularly high isocyanate contents can be present, as is the case, for instance, when welding. Of all the dangerous substances on the limit value list, isocyanates have the lowest permissible contents. Exposure to this new type of isocyanates was previously unheard of. Isocyanates in both gas and particle phase have been detected in connection with welding, grinding and cutting of painted automobile sheet steel, and respirable particles in high contents containing isocyanates have been detected. In thermal decomposiion products of painted automobile sheet steel, detection has been made of, among other things, methyl isocyanate (MIC), ethyl isocyanate (EIC), propyl isocyanate (PIC), phenyl isocyanate (Phi), 1,6-hexamethylene diisocyanate (HDI), isophorone diisocyanate (IPDI), 2,4- and 2,6-diisocyanate toluene (TDI) and 4,4-methylene diphenyldiisocyanate (MDI).

In thermal decomposition of phenol/formaldehyde/urea-(FFU)-plastic, isocyanic acid and methyl isocyanate are formed. FFU plastic is used, among other things, in wood glue and as a binder in mineral wool (and bakelite), which is frequently used as insulation for ovens and furnaces in industrial and domestic use. New fields of application in which exposure to isocyanates has been detected are the soldering and processing of printed circuit boards in the electronic industry, the welding, grinding and cutting of painted sheet steel in the automobile industry and the welding of lacquered copper pipes. Isocyanates have a varying degree of toxicity to the organism depending on their chemical and physical form. As a result, the hygienic limit values have been set at an extremely low level in all countries. For the exposed individual, the degree of exposure to isocyanates varies considerably in different operations during a working day and in connection with breakdowns. Thermal decomposition products from PUR constitute a special problem, since new and completely unknown isocyanates are formed, whose toxicity has not yet been analyzed in a satisfactory manner. Furthermore, the increasingly sophisticated measuring methods have revealed exposure to isocyanates in an increasing number of operations in industry.

To sum up, there are a number of operations in numerous working areas where people are daily exposed to or at risk being exposed to isocyanates at a varying degree. Considering the ominous tendency of isocyanates to cause respiratory diseases and the fact that there are some carcinogenic substances among the thermal decomposition products of polyurethane, e.g. 2,4-diamine toluene (TDA), 4,4-methylenediamine (MDA) and MOCA, it is very important to measure in a reliable, sensitive and rapid manner any presence of isocyanates, but also other decomposition products dangerous to health, in environments where there is such a risk.

There is also a particular interest to moniitor and analyze such solid/liquid air pollutants as asbestos, dust, metals, bacteria, oil mist, and fungi.

There is also a need to monitor and analyse certain chemical substances present in liquids, e.g. drinking-water, and flows in connection with purification plants. In such cases the liquid flow is transported through a sampling device in which the chemical to analyze is adhered to a specific reagent immobilized within the sampling device, e.g. in a filter and/or on the inner walls thereof.

A sampling device for analysis of air pollutants, more precisely poluretane products, is disclosed in WO 00/75622, and further developments thereof are disclosed in WO 2011/108981 and in WO 2007/129965. The sampling devices, also called samplers, disclosed in these publications collect the probed chemical in a two-step process. A fluid in which the amount of a chemical is to be measured is pumped through the sampling device using a controlled flow. The chemical substance of interest present in the gas phase of the fluid is collected in an adsorption tube using a regent coated on the surfaces present inside the tube. The flow of fluid is further pumped from the adsorption tube to and through a filter impregnated with the same reagent. The chemical substance in solid form or adhered to particles in the fluid is collected in the filter. After the measurements have been performed, the sampling device is sealed and is shipped to a laboratory for analysis of the amounts of chemical substance collected during the measurements.

However, it is very important that the sealing of the filter of the sampler is fluid-tight and secure for the measurement to be reliable. If leakage occurs during the measurement in such a way that the gas flow may circumvent the filter, the measurement will be inaccurate. Currently used samplers show some structural drawbacks. E.g. the filter is held in place by a filter holder and is in contact directly with an abutment portion of the filter holder. By rotating either the filter holder or the adsorption tube, or both, when assembling the sampler components, the filter may be sheared or broken due to the rotational forces induced, and leaks may occur. The filter may also unintentionally shift in position during the rotation of the sampler components creating large gaps around the filter, thereby making the measurement inaccurate.

A further problem is that when storing the assembled sampler, the pressure exerted on the filter may alter due to ageing of the filter. Thereby the sealing properties may be negatively affected.

Before and after a sampling session has been performed it is also important that the sampling device is protected from the outside environment with a view to avoiding contamination via diffusion of undesired substances into the sampler. Therefore, it is important to use sealing caps in the inlet and outlet ends, in particular in the inlet end of the sampler when the sampler not is in use, e.g. during transport. Otherwise, the measurements may be negatively affected and destroyed by the undesired diffusion into the sampler. Thus, as sampling in several environments may be very expensive and require highly accurate measurement results, it is of great importance that the sampler is fluid-tight against the outside environment when assembled, in particular during handling and transport before and after the measurements. Traditionally, interior caps of plug type have been used since they are simple, air-tight and robust. Interior caps need interior wall surfaces on the adsorption tube to abut to with a view to being able to create a fluid-tight sealing. However, on these inner wall surfaces adsorbed substances that are intended to be analyzed will stick to the surface of the cap and will then be excluded from the analysis when the cap is taken off at the analysis laboratory.

A further problem in connection with the use of caps is that when they are removed and placed nearby the sampler during the measurements, they may adsorb substances on their surfaces. When the caps are attached to the sampling device, the substances adsorbed on the surface of the inlet cap which is in contact with the interior of the sampling device may be desorbed and then instead be adsorbed in the adsorption tube, thereby disturbing the measurement result. Correspondingly, substances adsorbed in the surface of the outlet cap which is in contact with the interior of the sampling device may be desorbed and instead then be adsorbed on the bottom surface of the filter, thereby also disturbing the measurement results. Caps that are removed and placed nearby the sampler during measurements may also be lost, and it may also take time to find them after a finished measurement, allowing time for undesired diffusion into the adsorption device. The latter is especially a problem in rough conditions, e.g. at measurements in cold places, where gloves are used, or at sea, where waves may make practical chores harder.

There is also a problem in connection with the use of sampling devices made by a standard polymer material or other no anti-static material in that air sampling through a non-conductive sampling device can create an electrical static charge to develop on the surfaces of the sampling device. The static charge will attract the particles of interest to collect onto the wall(s) of the sampling device instead of being collected by the filter medium contained in the air sampling device that was designed to retain the particles of interest. When the filter medium is removed from the sampling device with a view to being analyzed, the particles of interest remain attached to the electrostatically charged device. This creates incomplete recovery of the sample, since particles of interest are left behind in the sampling device, and these wouldn't be analyzed. This problem creates an inaccurate concentration determination from the collected air sample.

The rate at which the electrostatic charge is created is highly variable, with variables being the following: the relative humidity of the air being sampled (as the relative humidity decrease, the electrostatic charge increases). The amount of the electrical charge of the particle itself will vary. The charge can be created depending on how the particle(s) becomes air-borne, and how long the particle(s) has been suspended in air. The speed at which the particles enter the sampling device can affect the electrical static charge that is buildt up on the surfaces of the sampling device.

Another problem in connection with use of sampling devices for the measurement of air-borne compounds in a fluid flow is the risk that the sampling device is tampered or manipulated during handling thereof, i.e. during the period from when it is transported from the supplier or the analysis laboratory to the user, is subjected to the sampling step by the user, and then is transported from the user to the analysis laboratory. When the sampling device is sent from the supplier or the analysis laboratory to the user, the filter is located within the sampling device, fluid tightly secured between the adsorption device and the filter holder. During the sampling step and the subsequent transport of the sampling device to the analysis laboratory the filter must be located within the sampling device all the time, i.e. the adsorption device and the filter holder may not be separated from each other. However, it has turned out that sampling devices have been manipulated or tampered with during the transports or by the user before, during, and after the sampling step, either unintentionally or intentionally. E.g., it has happened that the adsorption device has been separated from the filter holder during the transport of the sampling device to and from the user or by the user at the sampling site. In such a case the filter becomes exposed to air-borne components from other sites than the sampling sites and also during indefinite time periods. This of course leads to false or inaccurate analysis results in the end. The reason for such a manipulation could be that it is made by mistake or with a view to intentionally provide a different analysis result than the correct one. It has also happened that the filter has been exchanged with another filter containing the intended analyte components, i.e. reaction products, in intentionally wrong concentrations or having other compounds bound thereto.

Another problem is that when the sampling device has been used once it is further used one or more times after the analysis step of the laboratory. E.g., when the adsorption device has been separated from the filter holder and the filter has been taken out for analysis, it has happened, unintentionally or intentionally, that a new filter has been introduced in the filter holder and that the adsorption device thereafter has been connected to the filter holder, thereby creating a sampling device for repeated use. When such a sampling device is sent to a user for sampling, the interior surfaces thereof normally are contaminated with different compounds from the previous sampling, and the analysis results finally obtained at the analysis laboratory will be false or inaccurate. Such a manipulation can be made by mistake, e.g. when the different parts of the sampling device appear to be unused, or, in the intentional case, with a view to saving money by reuse thereof. U.S. Pat. No. 5,601,711 discloses a filter device for separation of materials, wherein it comprises two or more inline tubular elements, one or more of which is a module that houses a filter medium. The elements may have complementary connection structures, e.g. an o-ring, compression connections, bayonet connections, snap connections, and the like.

US 2010/0010455 discloses a medical delivery system adapted to be locked axially and unlocked rotationally.

US 2009/0242470 discloses a filter closure system having a connecting end and a connecting head which have a bayonet connection with receiving slots or receiving projections and matching insertion projections.

Thus, there is a clear need to provide an improved sampler containing a filter that is fluid-tightly sealed without risk of any leakage around the edges of the filter. Further, there is a need for an improved sampler with a view to avoiding contamination from its surroundings during handling and transport of the sampling device and for a sampler having caps that are not lost during measurement and that not may contaminate the sampling device by the surroundings.

Thus, there is also a need for a way to prevent manipulation and tampering of the sampling device during the transport from the supplier or sampling laboratory to the user, by the user in connection with the sampling step, and during the transport from the user to the analysis laboratory. There is also a need to prevent use of the sampling device more than once.

SUMMARY OF THE INVENTION

An object of the present invention is to eliminate the above-mentioned problems and provide a fluid-tightly sealable sampling device for environmental, laboratory and medical analysis, wherein improved sampling with higher liability in a fluid flow for the analysis of one or more substances of interest is provided and wherein the risk of manipulation and reuse of the sampling device is reduced or eliminated.

According to the invention, this object is achieved by means of a fluid-tightly sealable sampling device comprising an adsorption device 1 which is hollow and is adapted to be provided with one or more reagents for adsorption of and reaction with said one or more substances in the a flow, a filter holder 2, which is hollow and is connected in a fluid-tight way with the adsorption device 1, a filter device 4 adapted to be provided with one or more reagents for adsorption of and reaction with said one or more substances in the fluid flow, a gasket 5 provided with at least one projection 6 engaged with at least one corresponding receiving slot in the filter holder 2, a first external cap 9 detachably connectable with the inlet end of the sampling device in a fluid-tight way, a second external cap 13 detachably connectable with the outlet end of the sampling device in a fluid-tight way, wherein the bottom surface of the gasket 5 abuts the top surface of the filter device 4, and the top surface of the gasket 5 abuts the lower edge surface of the adsorption device 1, and wherein the adsorption device 1 is locked to the filter holder 2 with a first sealing connection means 3 in such a way that forces only axial in relation to the fluid flow direction are exerted by the gasket 5 on the filter device 4 during assembling and handling of the sampling device.

In a further aspect the object of the present invention is achieved by means of a fluid-tight sealable sampling device comprising a filter holder 2, which is hollow, a filter device 4 adapted to be provided with one or more reagents for adsorption of and reaction with one or more substances in a fluid flow, a gasket 5 provided with at least one projection 6 engaged with at least one corresponding receiving slot in the filter holder 2, a first external cap 9 detachably connectable with the filter holder 2 via a distance piece in a fluid-tight way, a second external cap 13 detachably connectable with the outlet end of the sampling device in a fluid-tight way, wherein the bottom surface of the gasket 5 abuts the top surface of the filter device 4, and the top surface of the gasket 5 abuts the lower edge surface of the distance piece, and wherein the first external cap 9 is locked to the filter holder 2 with a first sealing connection means 3 in such a way that forces only axial in relation to the fluid flow direction are exerted by the gasket 5 on the filter device 4 during assembling and handling of the sampling device.

Specific embodiments of the sampling device are defined in the dependent claims.

In another aspect the present invention relates to a method for an improved measurement of a fluid flow for analysis of one or more substances, wherein a) a fluid-tightly sealable sampling device according to the present invention is provided at a measurement spot, b) the first external cap 9 and the second external cap 13 are detached from the ends of the sampling device and are connected in such a way that the inner surfaces of both of the caps 9 and 13 are sealed in a fluid-tight way, c) the fluid flow is calibrated by drawing it into a calibration flow inlet 22 in the upper end of the calibration nozzle 10, through the sampling device, and out from a fluid exit 18 in the lower end of the filter holder 2 during a predetermined period, d) the calibration nozzle 10 thereafter is detached, e) the fluid flow to analyze is drawn into a fluid inlet 17, through the sampling device, and out from the fluid exit 18 during a predetermined period, f) the first external cap 9 and the second external cap 13, respectively, thereafter are attached to the ends of the sampling device in a fluid-tight way, and g) the amount of said one or more substances having reacted with the reagent in the sampling device is determined.

The present invention also relates to use of the sampling device in laboratory and/or medical analysis methods in which exact measurement results are of importance.

DETAILED DESCRIPTION OF SPECIFIC EMBODIMENTS

The expression "one or more substances" used throughout the application text means that two or more different substances in the fluid flow may be adsorbed by and react with one or more reagents at the same time within the sampling device. This is dependent on the choice of reagent or mixture of reagents present in the sampling device. In the following, the expressions "substance" and "substances" are sometimes used for simplicity reasons, but is nevertheless intended to mean "one or more substances", unless otherwise is indicated or appears from the context.

The expression "one or more reagents" used throughout the application text is intended to mean that more than one type of reagent may be used when more than one type of substance in the fluid flow is to be analyzed. In the following, the expressions "reagent" or "reagents" are sometimes used for simplicity reasons, but is nevertheless intended to mean "one or more reagents", unless otherwise is indicated or appears from the context.

The expression "fluid flow direction" used throughout the application text is intended to mean the axial direction in relation to the cross-section of the adsorption device (1) and the filter holder (2).

The expression "fluid flow" used throughout the application text is intended to mean a flow of a gas or a liquid, which also may contain components in solid form, e.g. fluidized particles and aerosols. One example of a fluid is an air flow containing small particles having the substances to analyze bound to their surfaces. Another example of a fluid flow is a water flow containing the substances to analyze, e.g. a drinking water flow, and flows in connection with purification plants.

Figure 1:
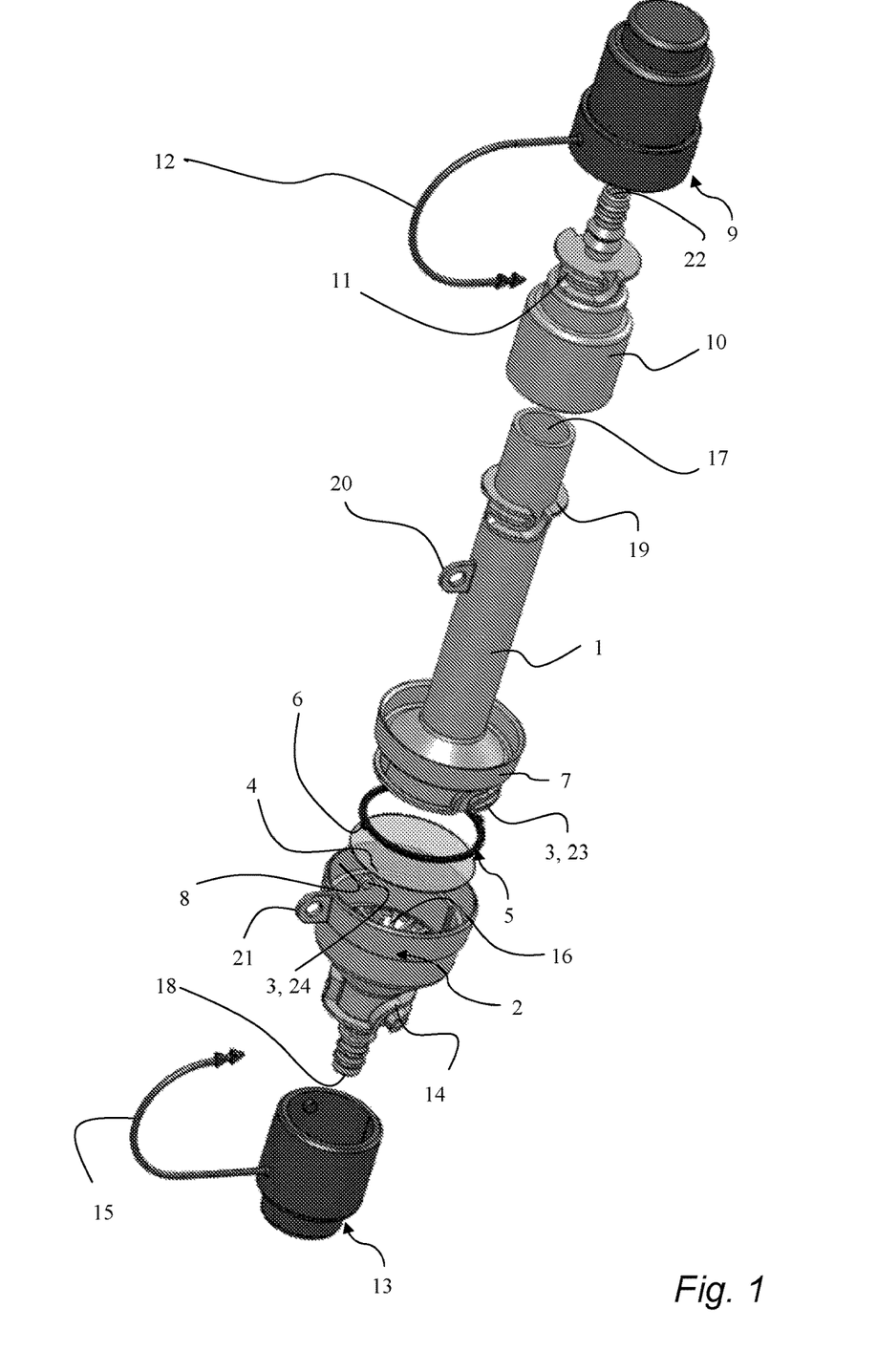
FIG. 1 schematically shows in an exploded view the different components of the fluid-tightly sealable sampling device according to the present invention.

The present invention will now be disclosed more in detail with reference to FIG. 1, which shows one embodiment of the fluid-tightly sealable sampling device in an exploded view. More precisely, FIG. 1 shows the different components of the sampling device before they are assembled to the final product.

The fluid-tightly sealable sampling device according to the present invention, in the following sometimes only referred to as "the sampling device according to the present invention" or "the sampling device", comprises a hollow adsorption device 1, and in the specific embodiment shown in FIG. 1, it is elongated and based on a tubular construction. The proportion of the length to the inner diameter is more than 4, preferably about 10. Such an adsorption device 1, which also may be called a "denuder", can have a length of 1 cm to 1 m and an inner diameter of 0.1 mm to 2 cm. The adsorption device 1 may be made of plastic or any other low-weight material. The inner cross-section of the adsorption device 1 may have any geometry as long as a satisfactory fluid flow through the adsorption device 1 is provided, e.g. a circular cross-section or a deviation thereof, e.g. an oval cross-section. The adsorption device 1 is adapted to be provided with one or more reagents for the reaction with the substances to analyze. The reagent may be immobilized on the inner walls of the adsorption device 1. Examples of such immobilization techniques are disclosed in detail in WO 00/75622.

Alternatively, the adsorption device 1 may contain a bed or a plate of packed beads or particles, e.g. made of glass, silicon dioxide or plastic, on which the reagent has been immobilized. The dimensions of such a bed are not critical, but it is preferably formed as a flat cylinder. In another embodiment the inner walls of the adsorption device 1 may be covered with silica particles with a view to increasing the accessible surface for the immobilization of the reagent, and thereby also for the adsorption and reaction of the substances to analyze.

In still another embodiment the reagent is not immobilized on the inner walls of the adsorption device 1. Instead, the reagent is immobilized on one or more elongated structures, e.g. slices of filter papers, which may be placed within the bore of the adsorption device 1. Said elongated structures may be folded, twisted or creased with a view to increasing the adsorption surface. In a further embodiment the reagent may be immobilized on both the inner walls and on said one or more elongated structures.

In still a further embodiment the adsorption device 1 contains or has been replaced with two or more parallel smaller, preferably elongated, adsorption devices. Thereby, the adsorption surface in the sampling device is further increased. During the measurement the fluid flow may then be drawn through all of these smaller adsorption devices at the same time. Each one of the smaller adsorption devices may contain one or more different reagents. Thereby, several different substances in the fluid flow may be adsorbed in the adsorption device 1 during the same measurement. The reagent may also be immobilized on the outside of each one of the smaller adsorption devices when they are contained within a larger adsorption device 1.

In one embodiment of the sampling device according to the present invention the adsorbent device 1 is not yet provided with reagent. In another embodiment, the adsorption device has been provided with reagent in any one of the variants disclosed above. E.g., a sampling device may be transported to the measurement site in an assembled condition but without any reagent therein. Thus, the sampling device may be opened in situ and be provided with reagent just before use. Alternatively, the sampling device is transported to the measurement site as assembled and already provided with reagent.

As shown in the embodiment in FIG. 1 the sampling device may comprise a hollow calibration nozzle 10, which in its upper end is provided with a calibration flow inlet 22 opening for the fluid flow. The calibration nozzle 10 may be connected with the upper end of the adsorption device 1 in a stable and fluid-tightly sealable way by use of a fourth sealing connection means 19, e.g. a bayonet connection, a snap connection, a thread connection, or any similar connection means. Before a measurement step is performed a calibration of the fluid flow through the sampling device must be performed. During the calibration step the fluid flow to analyze is drawn in through the calibration flow inlet 22 in the upper end of the calibration nozzle 10, through the whole sampling device and out therefrom by use of a pump (not shown in FIG. 1) connectably attached to the calibration nozzle 10. When the calibration step has been finished, the calibration nozzle 10 is detached from the adsorption device 1 and may then be discarded. During the subsequent measurement step the fluid flow is introduced in the adsorbent device 1 via a fluid inlet 17. The calibration nozzle 10 may also be detached from the adsorption device 1 in the case the adsorption device 1 is to be provided with a reagent before the calibration step at the measurement site. In one embodiment the sampling device does not comprise any calibration nozzle 10, and in that case the calibration is performed by introducing the fluid flow directly in the fluid inlet 17 of the adsorption device 1 via a hose having a substantially larger diameter than the diameter of the calibration flow inlet 22.

When using the sampling device for an air flow containing a gas phase and a particle phase containing said one or more substances which are to be analyzed, the air flow is allowed to pass through the adsorption device 1, wherein the major content of the substances in the gas phase first are adsorbed on and subsequently react with the reagent which is immobilized within the adsorption device 1. However, the portion of the substance which is bound on and/or within air-borne particles in the fluid flow is passed through the adsorption device 1 and reaches a filter together with a small portion of the substance in the gas phase which has not been adsorbed.

Thus, the sampling device according to the present invention also comprises a filter device 4, which is not critical as to its dimensions, but is in one embodiment, as shown in FIG. 1, formed as a substantially flat cylinder having an inner diameter which is greater than that of the inner cross-section of the adsorption device 1. In the case of a gas flow to analyze, the filter device 4 can be of any type which provides a separation of the particle phase and the gas phase in the gas flow and is, for instance, made of a glass, metal or plastic material having a pore diameter of about 0.1-20 μm, preferably 0.3-0.5 μm. E.g., the filter device 4 may be provided with a reagent in the same way as the adsorption device 1. The filter device 4 may be impregnated with a solution containing the reagent, which then is immobilized in the filter structure. Substances in the particle phase, i.e. that are present on or within the air-borne particles, in the passing fluid flow are dissolved from the particles in the filter device 4 and react in the same way with the immobilized reagent. In the case of DBA as reagent for the reaction with and binding of isocyanates, the binding reaction takes place immediately and is not affected by interfering substances in the sample.

In the case the fluid flow is a liquid flow, e.g. a drinking-water flow, the filter device 4 and the adsorption device 1 has to be dimensioned in such a way that a too high pressure drop is avoided.

The sampling device according to the present invention may be connectable with a pumping or suction device (not shown in the Figs.) which can be of any type providing the required passage of the fluid flow through the sampling device, but it is preferably a suction device in the form of a vacuum tube or a displacement pump, such as a hose pump, diaphragm pump, injection pump or gear-type pump. In a specific embodiment, this device is arranged in the lower end of the sampling device. In addition, the pump or suction device should not be integrated in the sampling device, but be usable more than once in contrast to a disposable sampling device. Furthermore, it should be provided with a measuring device for determining the desired amount of fluid that is to pass. This amount is controlled by the permissible value limit for the substance involved. The pump or suction device can also be calibrated or adjusted so that the passage of fluid is controlled in such a manner that a constant fluid flow is obtained during the time of sampling. This is made during the calibration step disclosed above, and during that step the pumping or suction device is connected to the calibration nozzle 10 located in the upper part of the sampling device.

The sampling device according to the present invention also comprises a hollow filter holder 2 having a design which makes it possible to receive the filter device 4 in its upper end. The inner cross-section of the filter holder 2 may have any geometric form that allows a satisfactory passage of the fluid flow. In a specific embodiment, as shown in FIG. 1, this cross-section is circular, and in that case it has an inner diameter which is larger than or equal to the diameter of a filter device 4 also having a circular cross-section. In a specific embodiment the circumferential edge surface of the filter device 4 abuts the inner wall of the filter holder 2 as tight as possible.

The filter device 4 is supported by a filter support 16 located within the filter holder 2. The filter support 16 may have any form as long as it allows a satisfactory passage of the fluid flow through the filter holder 2. In the embodiment shown in FIG. 1, the filter support comprises several radially extending projections, each one attached to the inner wall of the filter holder 2 and running towards the center of the inner cross-section of the filter holder 2, ending close to the center of the inner cross-section. Such a filter support 16 is made of a material which is strong enough to support the filter device 4 in a stable way, while it at the same time occupies a smaller part of the inner cross-section area within the filter holder 2, thereby allowing a satisfactory fluid flow.

As disclosed above, filters in conventional sampling devices are subjected to detrimental forces induced by the direct contact between a part of the filter and the lower edge surface, which often is circumferential, of the adsorption device. E.g., such filters may be deformed, break into pieces or be subjected to cracks. Further damage of the filters is obtained when rotational forces are applied on the filters, e.g. when adsorption devices are connected with filter holders via e.g. threads, which include a screwing moment. This can lead to leakage of the fluid flow between the circumferential edge surface of the filters and the inner wall of the corresponding filter holder, wherein some of the substances to analyze not are bound in the filters, but are instead emitted from the exit of the sampling device. Further, if the filters are damaged, undesired leakage of substances to analyze through the filters takes place. Thereby, an inaccurate or unreliable result of the measurement is obtained.

Therefore, the sampling device according to the present invention also comprises a gasket 5 or another packing means, which is intended to protect the filter device 4 from the action of the lower end of the adsorption device 1. In the embodiment shown in FIG. 1, illustrating a circular inner cross-section of the sampling device, a gasket in the form of an O-ring is used.

The design of the gasket 5 may be based on any commercially available gasket having the resilient, cushioning, and tightening properties desired. The gasket 5 may, however, also be rigid and act more as a support ring for supporting the lower edge of the adsorption device 1 and take up any rotational forces so that the filter is not subjected to rotational forces. The design should be adapted to the cross-section of the filter device 4, and to the inner cross-section of the adsorption device 1 and the filter holder 2, respectively. In the embodiment shown in FIG. 1 the gasket 5 is based on an annular shape, e.g. a conventional O-ring. However, with a view to further protecting the filter device 4 from detrimental rotational forces in connection with assembling, handling, and transport of the sampling device, the gasket 5 is provided with one or more projections 6. Said projections 6 are intended to engage in receiving slots (not shown in FIG. 1) located in the inner wall of the filter holder 2. Said one or more projections 6 protrude from the circumferential edge surface of the gasket 5 and may be integrated with the gasket 5, i.e. be produced in one piece and in the same material. In the embodiment shown in FIG. 1 the gasket 5 is provided with two projections 6, but three, four or more projections, preferably evenly distributed around the circumferential edge surface of the gasket 5, may also be used. During the step of assembling the sampling device the gasket 5 is applied on the filter device 4, which is supported by the filter support 16 in the filter holder 2, in such a way that the annular lower surface of the gasket 5 abuts a peripheral part of the top surface of the filter device 4. When the lower circumferential edge surface of the adsorption device 1 abuts the annular upper surface of the gasket 5 and the adsorption device 2 is connected with the filter holder 2, the filter device 4 is subjected to axial forces in relation to the fluid flow direction. Although the filter device 4 may be subjected to rotational forces during the assembling step, it may be subjected to minor rotational forces during transport and handling, which could induce dislocation of the gasket 5 and/or the filter device 4 and thereby potential damage. The projections 6 preclude or minimize such undesired rotational movement of the filter device 4.

The inner diameter of the upper part of the filter holder 2 is larger than the outer diameter of the lower part of the adsorption device 1. Therefore, the adsorption device 1 may be inserted in the filter holder 2, however with a specific tolerance, i.e. only a certain distance into the filter holder 2. This tolerance is pre-determined and is to be established by the constructor of the sampling device. It should be adapted to that axial force the adsorption device 1 exerts on the filter device 4 via the gasket 5. This force may not be so high that the filter device 1 is damaged, and also not so low that leakage between the abutting surfaces of the filter device 4 and the gasket 5, and of the gasket 5 and the adsorption device 1 would arise. This is, inter alia, accomplished with a frusto-conical flange 7 provided on the circumferential surface of the lower part of the adsorption device 1. Said frusto-conical flange 7 fits into a corresponding frusto-conical receiving part 8 provided on the inner wall surface of the filter holder 2. In one embodiment the upper part of the hollow filter holder 2 has a slightly frusto-conical shape as a whole, as shown in FIG. 1. When the adsorption device 1 is inserted with the pre-determined tolerance within the filter holder 2 during the assembling step, the frusto-conical flange 7 fits into the frusto-conical receiving part 8 in a fluid-tight way. This fluid-tight arrangement may be further secured by means of the principle of a conventional pipe connection securing device comprising an annular means having inner threads, said annular means being intended to be screwed on to threads provided on the outer surface of both the adsorption device 1 and the filter holder 2. At the same time an optimal axial force is exerted on the filter device 4 without risk of any detrimental effect on the filter device 4.

The adsorption device 1 may be locked to the filter holder 2 by the use of a first sealing connection means 3 having the ability to not exert any rotational or torsional forces on the filter device 4 via the gasket 5. The first sealing connection means 3 may be a conventional bayonet connection, a snap connection, a thread connection or any other similar means providing non directly rotational influence on the filter device 4. This rotation force induced is neglectable and does neither influence the position of the gasket 5 nor induce any rotation force by the gasket 5 on the filter device 4. In the case of a snap connection, the locking action is obtained by use of interacting projections and recesses in the filter holder 2 and the adsorption device 1, respectively, said projections and recesses engaging each other in a locking manner. The locking action of the first sealing connection means 3 in the case it is a bayonet connection is obtained via a slight rotation of the bayonet connection until a receiving part 3, 23 located on the circumferential surface in the end part of the adsorption device 1 reaches and is locked by a projecting locking part 3, 24 located on the circumferential inner surface of the filter holder 2. Thus, the first sealing connection means 3 comprises one receiving part 23 arranged on the adsorption device 1 and one locking part 23 arranged on the filter holder 2. In the case of the bayonet connection embodiment shown in FIG. 1, the receiving part 23 is a curved groove, and the locking part 24 is a pin to be received by the groove 23. In another bayonet connection embodiment the groove 23 is located on the filter holder 2 and the pin 24 on the adsorption device 1. The same principle as for a bayonet connection applies for a snap connection. In the case of the thread connection, the rotational movement would not involve contact of the adsorption device 1 with the gasket 5 at the early stage of the movement until the filter, the gasket 5 and the lower edge of the filter holder are very close. At this moment the gasket 5 will withstand the rotational force. Only an axial force is transferred to the filter, minimizing or avoiding the risk of damage to the filter.

In such a way a secure and fluid-tight connection between the adsorption device 1 and the filter device 2 is obtained providing for more exact and accurate analysis results. Thus, no fluid flow may pass between the abutting surfaces of the gasket 5 and the filter device 4. The fluid flow may only pass through the filter device 4 via the central part thereof.

Figure 4:
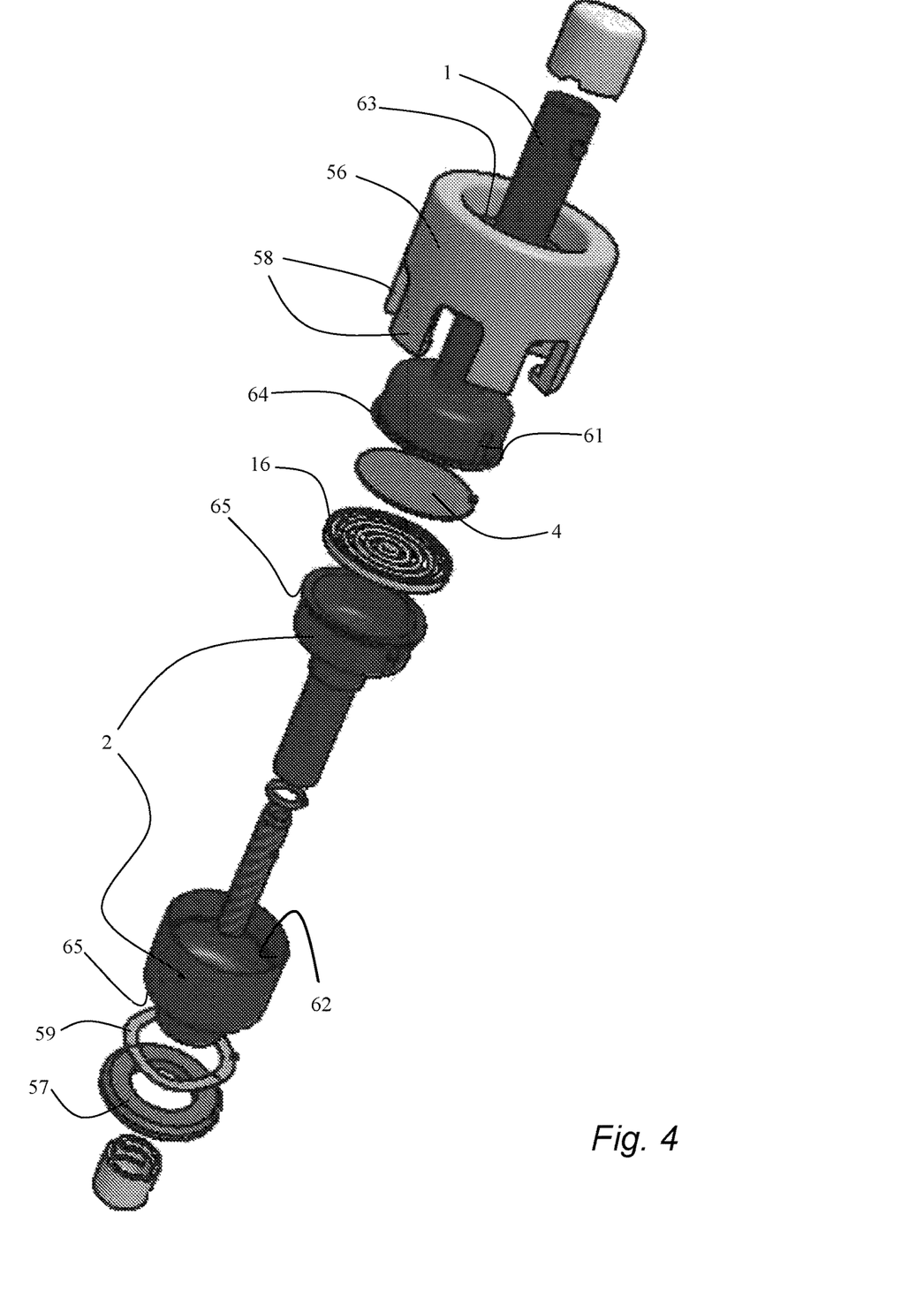
FIG. 4 schematically shows in an exploded view the different components of a further embodiment of the fluid-tightly sealable sampling device according to the present invention.
Figure 5:
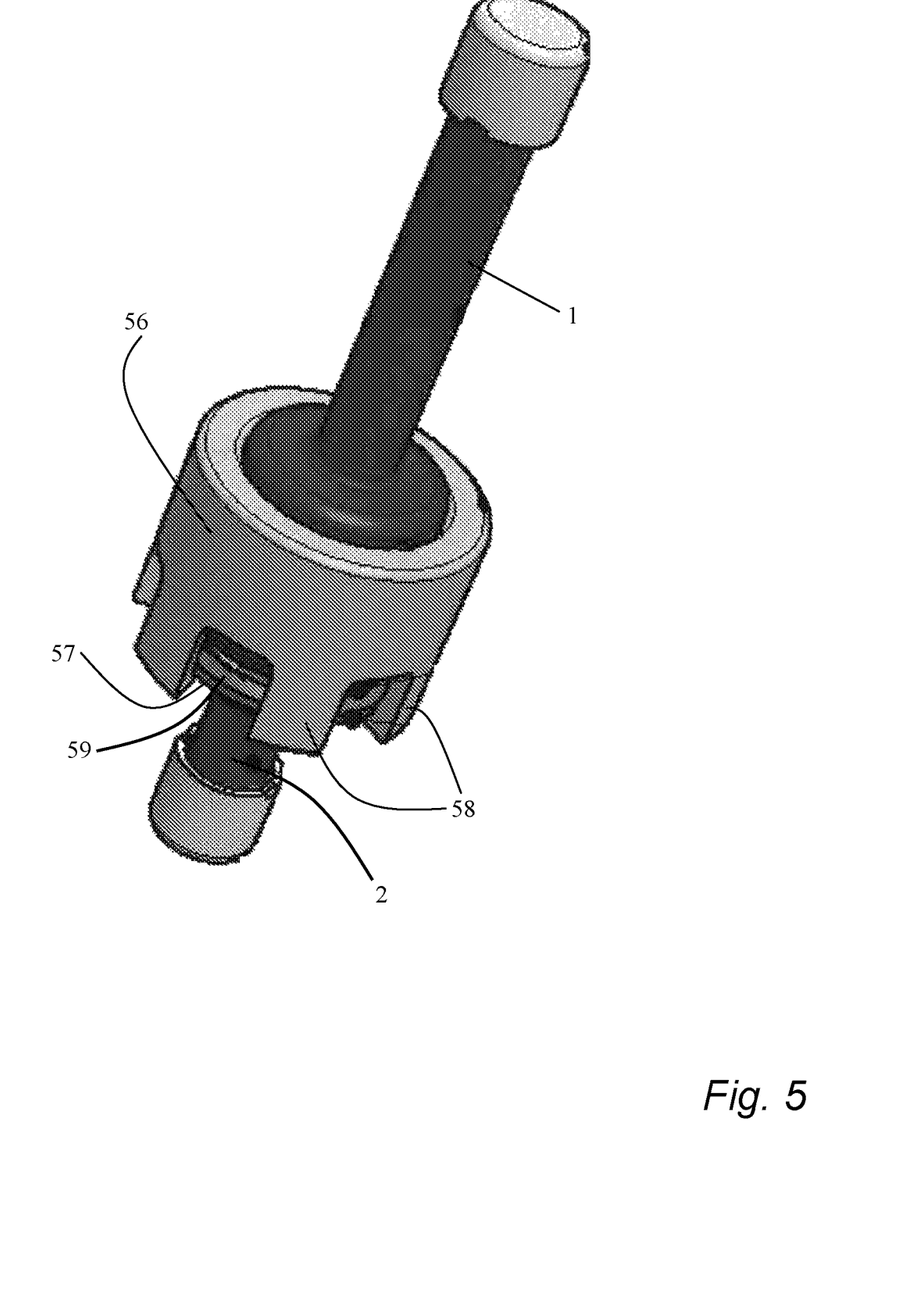
FIG. 5 schematically shows the fluid-tightly sealable sampling device of FIG. 4 as assembled.

In a further embodiment of the present invention, as shown in FIGS. 4 and 5, respectively, the first sealing connection means 3 of the sampling device is a sealing connection assembly comprising a first locking element 56 being adapted to at least partly enclose said adsorption device 1 and comprising at least one gripping element 58, a second locking element 57 being adapted to at least partly enclose said filter holder 2, wherein said at least one gripping element 58, preferably one or more clutches, of said first locking element 56 is adapted to sealingly engage said second locking element 57 thereby locking said adsorption device 1 and said filter holder 2 together, and said sealing connection assembly further comprises a resilient washer 59 arranged between said first locking element 56 and said second locking element 57.

In FIG. 4, the filter holder 2 is shown as two parts. These are functionally a unit and may therefore be integral to save manufacturing and assembling costs.

The gripping element 58 of the first locking element 56 preferably comprises more than two clutches, each of which are at least slightly bendable in the radial direction, so as to be able to be pressed over an edge of the second locking element 57 when assembling the sampling device.

The resilient washer 59 will provide a force between the first and second locking element 56, 57 so that the sealing connection assembly provides a sealed connection of the sampling device also if the materials in the sealing connection assembly are affected by temperature and pressure changes. The skilled person realizes that the resilient washer 59 can be any kind of resilient washer 59 to proving the force mentioned above as e.g. a spring washer, a spring, a resilient rubber structure etc. The resilient washer is preferably annular and is in one embodiment adapted to provide a pressure in the axial direction of the sealing connection assembly, said axial direction being the centre axis of the resilient washer 59.

Further or instead of said gasket 5 and said at least one projection 6, the sampling device comprises at least one protrusion 61 on the outer side of said adsorption device 1, said at least one protrusion 61 being adapted to be received in said slots of said filter holder 2, thereby preventing rotational movement between said adsorption device 1 and said filter holder 2. This will eliminate any risks of relative rotation between the adsorption device 1 and the filter holder 2 after that the sampling device has been assembled.

The sampling device may further comprise a third locking element (not shown) being adapted to at least partly enclose said filter holder 2 and being adapted to be arranged between said resilient washer 59 and said filter holder 2.

According to a further embodiment of the sampling device, said first locking element 56 is integral with said adsorption device 1 and/or said second locking element 57 is integral with said filter holder 2 so as to reduce the number of parts needed in the sealing connection assembly and thereby reduce the costs for manufacturing the parts for the sampling device and possibly making assembling the sampling device easier. The embodiment using the sealing connection assembly will now be discussed more in detail with reference to FIGS. 4 and 5. The sealing connection is accomplished using a sealing connection assembly 56-59 of FIG. 4 and FIG. 5, acting as a complement to the embodiment of FIG. 4. In this embodiment the sealing connection is established with a sealing connection assembly used for the sampling device. The adsorption device 1, the filter holder 2, the filter device 4, and the filter support 16 are pressed together in a fluid tight manner by the first locking element 56 gripping the second locking element 57 with clutches 58 in a snap-in connection where the clutches 58 grip around the second locking element 57. The resilient washer 59 is compressed between the second locking element 57 and the filter holder 2 so as to inflict a force in the axial direction of the sealing connection assembly and the sampling device. The annular first locking element 56 has an annular edge 63 working as a seat for an annular edge 64 of the adsorption device 1. The filter holder 2 has a corresponding annular edge 65 for receiving the resilient washer 59 and the second locking element 57.

In FIG. 4 it is also shown that protrusions 61 on the adsorption device 1 are adapted to engage the slots of the filter holder 2 so as to eliminate any possibility of relative rotation around the axial direction between the adsorption device 1 and the filter holder 2.

In FIG. 4 the filter holder 2 an adsorption device 1 is shown having a filter paper adjacent its inner wall. The sealing connection assembly is thus used for the sealing of a sampling device through which a fluid flow may be drawn by a suction pump (not shown) connected to the filter holder 2. Substances and/or particles in the fluid flow may then be sampled either by being collected by the filter device 4 or being adsorbed to the filter device 4 in the adsorption device 1.

In FIG. 5 the sealing connection assembly of FIG. 4 is assembled. It is visible how the clutches 58, in a snap-in connection, grip around the second locking element 57. The resilient washer 59 is compressed between the second locking element 57 and the filter holder 2 applying a sealing force in the axial direction of the sealing connection assembly and the sampling device. The annular edge 63 of the first locking element 56 works as a seat for the annular edge 64 of the adsorption device 1. The annular edge 65 of the filter holder 2 receives the resilient washer 59 and the second locking element 57.

The sampling device according to the present invention is also provided in its upper inlet end with a first external cap 9 and in its lower outlet end with a second external cap 13. In the following, the shorter expressions "cap 9" and "cap 13" are instead sometimes used for simplicity reasons. In the embodiment shown in FIG. 1, the first external cap 9 is detachably connected with the calibration nozzle 10 and covers the calibration fluid inlet 22 thereof. The second external cap 13 is detachably connected with the lower outlet end of the filter holder 2 and covers the fluid exit 18. As stated above, it is of great importance that the interior of the sampling device not becomes contaminated with undesired substances which may disturb the analysis result, e.g. by giving rise to undesired reactions with the reagent. Therefore, the first external cap 9 and the second external cap 13 are attached to the inlet and the outlet end, respectively, of the sampling device during the transport to and from a measurement site. Just before the initial calibration step, the caps 9 and 13 are detached from the ends of the sampling device, the first external cap 9 from the upper part of the calibration nozzle 10 and the second external cap 13 from the lower part of the filter holder 2. Clean air as calibration flow is then drawn through the sampling device until the calibration has been made.

The expression "external cap" used throughout the application text, i.e. in the expressions the first external cap 9" and the second external cap 13", is intended to mean that the cap is attached to the ends of the sampling device in such a way that none of the surfaces of the caps 9 and 13 comes in contact with any inner surface of the sampling device. It is of particular importance that the inner wall surface of the adsorption device 1 not becomes contaminated, but contamination of the inner walls of the filter holder 2 should also be avoided. Instead, the inner surfaces of the caps 9 and 13 abut the circumferential surface of the upper and the lower part of the sampling device, respectively, i.e. only the outside thereof, in such a way that only outer surfaces of the sampling device are contacted by the caps 9 and 13.

The caps 9 and 13 are detachably connected with the sampling device in a fluid-tight way by insertion, in each of the caps 9 and 13, of the corresponding receiving part of the sampling device, i.e. the upper part of the calibration nozzle 10 (before calibration) or the adsorption device 1 (after measurement), and the lower part of the filter holder 2, respectively. This means that the inner diameter of the open end of the first external cap 9 is approximately the same as, but not smaller than, the outer diameter of said receiving part on both the calibration nozzle 10 and the adsorption device 1, wherein a fluid-tight sealing is obtained when the receiving part in question is inserted into the open end of the first external cap 9. The first external cap 9 may also be locked to the calibration nozzle 10 in a secure and stable way by use of a second sealing connection means 11, e.g. a bayonet connection, a snap connection, a thread connection, or any other similar sealing means. Further, after the measurement step the first external cap 9 may be locked to the upper part of the adsorption device 1 with a fourth sealing connection means 19, e.g. a bayonet connection, a snap connection, a thread connection, or any other similar sealing means. The second external cap 13 may be locked to the filter holder 2 with a third sealing connection means 14. In view of the second, third, and fourth sealing connection means 11, 14, and 19, respectively, these have the same function as disclosed above for the first sealing connection means 3, and in the case of a bayonet connection, it contains a projecting pin intended to be received in a groove.

Figure 2:
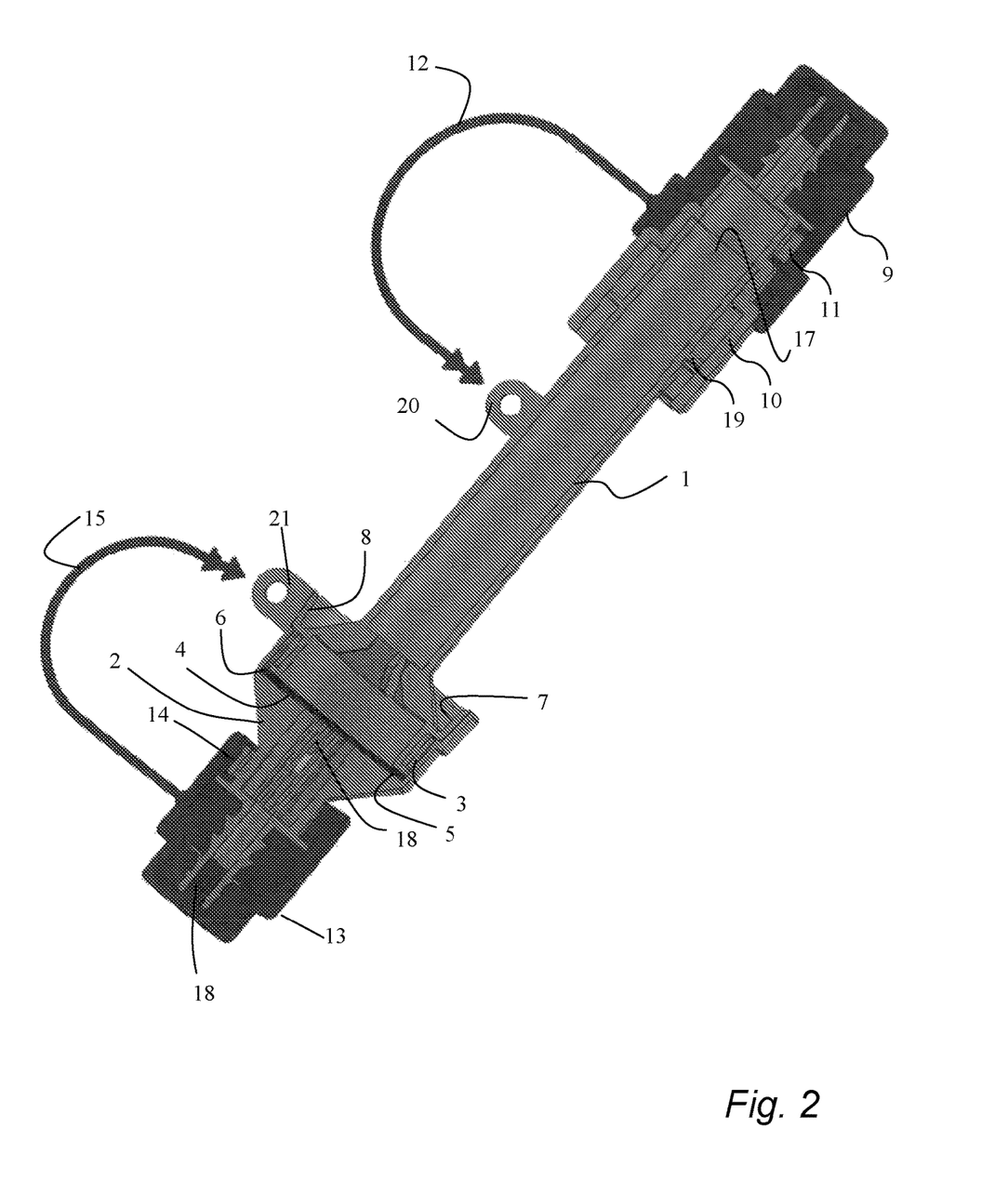
FIG. 2 schematically shows in a cross-section view the fluid-tightly sealable sampling device according to the present invention as assembled.

The caps 9 and 13 may have any specific form provided that they have the ability to fluid-tightly cover the inlet and the outlet of the adsorption device 1 and that no surface thereof comes in contact with the inner surface of the adsorption device 1. Thus, covers, lids, and other similar constructions fulfilling the requirement above may be used in the sampling device according to the present invention. In one embodiment, which is shown in FIG. 2, a projection extending upwards from the bottom surface of the first external cap 9 and the second external cap 13 may be provided in such a way that it may be fluid-tightly inserted into the calibration flow inlet 22 in the upper end of the calibration nozzle 10 and into the fluid exit 18 in the lower end of the filter holder 2, respectively.

Although external caps are included in the sampling device according to the present invention, it is desirable to further minimize the risk of contamination of cap surfaces which are exposed to undesired environmental substances during the measurement step. In one embodiment the first external cap 9 and the second external cap 13, when detached from the sampling device during the measurement step, are connectable with each other in such a way that the inner surfaces of said caps 9 and 13, respectively, are tightly sealed from the environment. For this purpose, the open end of the first external cap 9 may be inserted in the open end of the second external cap 13, or vice versa. This means that the outer diameter of one of the caps is smaller than the inner diameter of the other cap. In such a way, a fluid tight sealing between the caps is provided. When the measurement period is over and the sampling device is to be transported for analysis, the caps are detached from each other and are fluid-tightly attached to the sampling device. The first external cap 9 is attached to the upper part of the adsorption device 1 in such a way that the fluid inlet 17 is fluid-tightly covered. The second external cap 13 is attached to the filter holder 2 in such a way that the fluid exit 18 is fluid-tightly covered. The caps 9 and 13 can be attached to the sampling device and detached from the sampling device, as well as from each other, either in a manual or automated way.

In the embodiment of the present invention shown in FIG. 1, the first external cap 9 is also detachably connectable with the adsorption device 1 via a first fastener device 12, e.g. a string, rope, cord, wire or a similar thread-like device, wherein one end of the first fastener device 12 is attached to the outer surface of the first external cap 9 and the other end is detachably connectable with a first receiving means 20, e.g. a means to which said outlet end of the first fastener device 12 may be detachably secured, such as a loop. Said first receiving means 20 is located on the outer surface of the adsorption device 1. Alternatively, the first fastener device 12 may in one end be attached to the outer surface of the adsorption device 1 and in the other end be detachably connectable with the first receiving means 20, which in that case is located on the outer surface of the first external cap 9. In another embodiment one end of the first fastener device 12 is detachably connected with the first external cap 9 and the other end is detachably connected with the adsorption device 1.

Further, the second external cap 13 may be detachably connectable with the filter holder 2 via a second fastener device 15, e.g. a string, rope, cord, wire, or a similar thread-like device, wherein one end of the second fastener device 15 is attached to the second external cap 13 and the other end is detachably connectable with a second receiving means 21, e.g. a means to which said other end of the second fastener device 15 may be detachably secured, such as a loop. Said second receiving means 21 is located on the outer surface of the filter holder 2. Alternatively, the second fastener device 15 may in one end be attached to the outer surface of the filter holder 2 and in the other end detachably connectable with the second receiving means 21, which in that case is located on the outer surface of the second external cap 13. In a further embodiment one end of the second fastener device 15 is detachably connected with the second external cap 13 and the other end is detachably connected with the filter holder 2.

Thus, the caps 9 and 13 can be connected to each other when detached from the sampling device, as disclosed in connection with the embodiment disclosed above, and at the same time be connected to the sampling device via the fastener devices 12 and 15, respectively. In such a way, the risk that the caps of any reason are lost or disappears during a measurement period is eliminated. The first fastener device 12 and the second fastener device 15 are in one embodiment made in a durable material prohibiting break thereof during handling and transport.

In an alternative embodiment with a view to avoiding contamination of the caps 9 and 13, these can be made for one time use or disposable purpose. In this case, the caps 9 and 13 will not be attached at all to the sampling device after the sampling step. When the caps 9 and 13 are removed for sampling and their inner sides are exposed to the air, they will be disposed. Once the sampling is completed, a new pair of caps 9 and 13, identical to the disposed caps and present in a sealed bag, will be used.

When a substance of interest to analyze is adsorbed in the adsorption device 1 and/or in the filter device 4, it normally reacts with the reagent immobilized therein, wherein a reaction product is formed, still being adsorbed. During the analysis, it is the reaction product that is analyzed and the amount thereof is directly correlated to the amount of the substance of interest. Alternatively, the substance of interest to analyze is not reacted with the reagent. Instead, it may be bound to it as such via ion pair binding or be just physically bound, but such a substance is here also called reaction product for simplicity reasons.

In connection with the analysis of the content of reaction products of interest bound in the sampling device, the different components of the sampling device are detached in the embodiment when the reagent initially not was immobilized on the inner walls of the adsorbent device 1. The filter device 4 and the elongated structures, e.g. filter papers, or the beads or particles initially having immobilized reagent bound thereto are taken out and are placed in a specific fluid-tight container for transport to the analysis laboratory. In connection with the analysis, the reaction products bound in the sampling device are eluated from the filter device 4 and from the elongated structures, or from the beads or particles, by use of an appropriate eluation agent.

In the case the reagent initially was bound to the inner walls of the adsorption device 1, the substances or reaction products bound in the sampling device, i.e. on the inner walls of the adsorption device 1 and in the filter device 4, are eluated from the sampling device by addition of an appropriate eluation agent to the fluid inlet 17 and collecting the eluted reaction product after emission thereof through the fluid exit 18. The analysis of the reaction product of interest may be performed in any conventional way.

FIG. 2 shows in an exploded view one embodiment of the fluid-tightly sealable sampling device according to the present invention as assembled. In the embodiment shown, like in FIG. 1, the first fastener device 12 is not attached to the first receiving means 20, and the second fastener device 15 is not attached to the second receiving means 21. The sampling device shown in FIG. 2 may be provided with reagent or not in its interior. As stated above, the embodiment when the caps 9 and 13, respectively, are provided with a projection extending upwards from the bottom surface is shown in FIG. 2.

Figure 3:
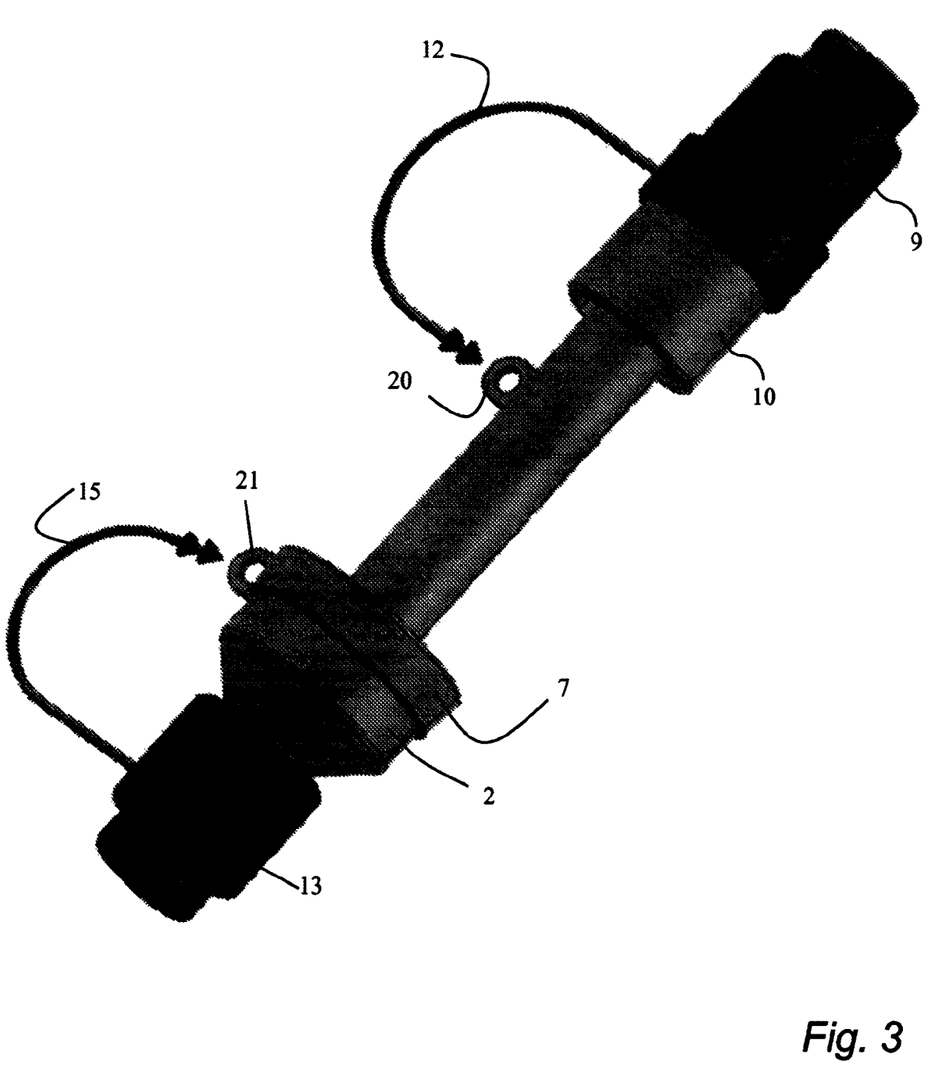
FIG. 3 schematically shows the fluid-tightly sealable sampling device according to the present invention as assembled.

FIG. 3 shows the same embodiment as in FIG. 2, but not in an exploded view.

In another embodiment the sampling device according to the present invention is also provided with a second adsorption device connected with a second filter holder (not shown in the Figs). In this embodiment the second adsorption device is fluid-tightly connected in its inlet end with the outlet end of the filter holder 2. The second filter holder is fluid-tightly connected in its inlet end with the outlet end of the second adsorption device. The outlet end of the second filter holder is detachably connectable with the second external cap 13 in a fluid-tight way. The second filter holder contains a second filter which is arranged in the similar way as the filter device 4 in FIG. 1, i.e. including a gasket with projections, a filter support, and sealing connection means. This embodiment is useful for the analysis of oil mist and volatile organic compounds (VOC). The adsorption device 1 and the filter device 4 in this embodiment are provided with at least one reagent but may also not be provided with a reagent. The second adsorption device and the second filter device may be provided with none, one or more different reagents compared to said at least one reagent in the adsorption device 1 and the filter holder 2.

Particles collected on the filter device 4 may contain volatile components. The volatile components may be volatilized and released from the filter and are then collected on the second adsorption device.

When the compounds bound to the above-mentioned filters and adsorption devices are to be analyzed, the different components of this embodiment of the sampling device are detached and are the kept and transported to the analysis laboratory in the similar way as the sampling device having only one adsorption device and only one filter, as shown in FIG. 1. Apart from the presence of the second adsorption device and the second filter holder, this embodiment of the sampling device may be provided with the same components and may be used in a similar way as the sampling device shown in FIG. 1.

In still another embodiment of the sampling device according to the present invention, the adsorbent device 1 has been eliminated. Instead, the substances of interest to analyze are reacted and bound directly on the filter device 4. This embodiment is not shown in the Figures. In principle, this embodiment may contain the same components as the sampling device shown in FIG. 1, except from the adsorption device 1 and the calibration flow nozzle 22. The first external cap 9 is connected with the filter holder 2 containing the filter device 4 via a distance piece, which is fluid-tightly connected with both the first external cap 9 and the filter holder 2. This embodiment of the sampling device is useful for the analysis of airborne solid pollutants, such as asbestos, dust, metals, bacteria, fungi, amines, alkanol-amines, aldehydes, ketones, acids, alkaline compounds, inorganic compounds, warfare agents and allergens. In this embodiment there is no need for an adsorption device 2, as these components are not volatile. Apart from the absence of the adsorption device 1 and the calibration flow nozzle 22, and from the presence of a distance piece, the sampling device according to this embodiment may be provided with the same components and may be used in a similar way as the sampling device shown in FIG. 1.

By means of the present invention, the total amount of the substance in question in the air flow can thus be quantitatively determined in a manner which is more accurate, reliable and safe than what previously has been possible. The reason for this is that the sampling device is more fluid-tight in its entirety, i.e. in the connections between the different components, in particular around the filter device, in the fluid inlet end, and in the fluid exit end. The influence of detrimental rotational forces during assembling of the sampling device has in principle been completely eliminated. Moreover, the risk for the entrance of contaminants into the sampling device, which could give rise to undesired reactions deteriorating the analysis result, is reduced compared to conventional sampling devices.

In another embodiment the fluid-tightly sealable sampling device is made of an anti-static or electrically conducting plastic giving it possibilities to avoid electrostatic charges that may be hazardous in some environments. E.g. the sampling device is made from polypropylene with carbon black added during the molding process with a view to making the sampling device electrically conductive. The conductive additive will reduce or eliminate the electrical static charge that can develop on the sampling device. This will reduce or eliminate the static attraction of the particles entering the sampling device while sampling. The particles of interest will then travel and become collected by the filter device 4 contained in the sampling device. Since no loss of particles occur to the wall(s) of the sampling device, all of the particles will be retained by the filter device contained in the sampling device. When the filter device 4 is removed from the sampling device for analysis, it contains all of the particles collected during the air sampling event. This results in an accurate concentration determination of the collected air sample.

According to one embodiment of the present invention, the problems with manipulation and reuse of a sampling device have been solved by providing the sampling device with a seal mechanism. The seal mechanism may be chosen from several known seal embodiments, but will be specifically adapted to the different embodiments of the sampling device according to the present invention. The main purpose of the seal mechanism is that it will make it visually evident or detectable if the sampling device has been manipulated or tampered with, i.e. if the adsorption device 1 has been separated from the filter holder 2 before the sampling device has reached the laboratory for analysis.

The seal mechanism is to be attached to or activated in the sampling device after the introduction of the filter device 4 therein. The introduction of the filter device 4 can be made by the producer, the supplier or the analysis laboratory before the sampling device is sent off to the user for sampling. Preferably, the seal mechanism is attached or activated by the analysis laboratory, which e.g. previously has inserted a pre-weighed filter in the sampling device.

There are two main kinds of useful seal mechanisms. The first kind is based on the sampling device defined in the claims, but having a complementary seal mechanism attached on the outer surface of the sampling device. The second kind is based on a modification of the first sealing connection means 3 disclosed in claim 1, including the receiving part 23 and the locking part 24, i.e. when the first sealing connection means 3 is a bayonet connection, snap connection, or a thread connection.

The first kind of seal mechanism includes a loop embodiment, wherein one loop is attached on the outer surface of the adsorption device 1 and one loop is attached on the outer surface of the filter holder 2, wherein the ends of a thread or a wire is attached to the loops in such a way that if the thread or wire is broken, it is not possible to repair it. In that way the analysis laboratory will know if the sampling device has been opened and in that case perhaps also tampered with.

The first kind of seal mechanism may alternatively be a clamping mechanism which is attached to the sampling device, e.g. by use of a clamping tool. The clamping mechanism will overlap the first sealing connection means 3, further making sure that the seal is not broken, but may also be made so that the clamping mechanism is impossible to open without destroying the clamping mechanism. The clamping mechanism may be made of a plastic having a locking mechanism that is not possible to open once it is locked, without breaking the clamping mechanism.

A further embodiment of seal mechanism of the first kind may be a seal that is read electronically from an external electronic reading device. The seal mechanism may be a small electronic connection, possible to connect only once, in analogy with the clamping device. The electronic connection may e.g. facilitate an electrically conductive structure comprising a simple RFIDtag, possible to read from a small distance. The electronic connection is preferably located inside the sampling device, so that it cannot be damaged or tampered with. It the sampling device is opened, the electrical connection is broken.

A still further embodiment of seal mechanism of the first kind may be a seal that is made from a tape covering the first sealing connection means 3. If the sampling device is opened, the tape is broken.

A still further embodiment of seal mechanism of the first kind may be a seal composed by a glue or adhesive, gluing the sealing connection means together, making it impossible to take apart. To facilitate a strong binding, the two parts of the sealing connection means 3 may have one component each of a two-component glue, e.g. an epoxy. The parts having pre-attached glue are preferably covered by a removable plastic strip that is intended to be removed when assembling the sampling device. The plastic strip will preserve the glue or adhesive and keep it from drying out.

The second kind of seal mechanism is based on a modification of the first sealing connection means 3 and includes a mechanical seal in the form of a part making the seal impossible to open without breaking it. A snap connection where e.g. a barb grips around an edge may be used. A weakening in the barb or the edge may be introduced, so that the seal mechanism may be opened while at the same time being destroyed which makes it evident if someone has tampered with the sampling device before it is sent back to the analysis laboratory. This seal mechanism may be incorporated in the first sealing connection means 3 of FIG. 1, where the pin 24 is replaced by a barb and a recess with a sharp edge is introduced at the end of the receiving part 23. The barb will then snap into the recess, where it will stay. A weakening in the barb so that it breaks if the sampling device is forced to be opened, will make sure that the sampling device may not be reused twice or more and it will be evident if the device has been opened.

With a view to further securing that the sampling device not is manipulated or tampered with during the transport from the user to the analysis laboratory, the seal mechanism can in one embodiment also be provided at the connection between the adsorption device 1 and the first external cap 9, as well as at the connection between the filter holder 2 and the second external cap 13. The seal mechanism may also be a modification of the third sealing connection means 14 and/or the fourth sealing connection means 19. In this embodiment the user mounts or activates the seal mechanism, e.g. when attaching the caps 9 and 13 after sampling, before the sampling device is forwarded to the analysis laboratory. In this embodiment both of the two abovementioned kinds of seal mechanisms may be useful.

The seal mechanism is also useful for attachment of the corresponding connection between parts of the sampling device in the embodiment comprising a second adsorption device and a second filter holder, as well as in the embodiment lacking the first adsorption device 1.

Thus, in one embodiment of the present invention the sampling device is provided also with a seal mechanism with a view to preventing manipulation and tampering of the sampling device during transport and in connection with sampling and with a view to preventing use more than once of the sampling device, wherein said seal mechanism is provided at the connection between the adsorption device 1 and the filter holder 2 in such a way that it is visually evident or detectable if the adsorption device 1 has been separated from the filter holder 2 between the step of assembling of the sampling device and the analysis step.

More precisely, the seal mechanism is either chosen from a) a seal mechanism attached on the outer surface of the sampling device or b) is a modification of the first sealing connection means 3, wherein the first sealing connection means 3 will permanently lock the sampling device, the first sealing connection means 3 having a structural weakness with a view to enabling opening of the sampling device by breaking the structural weakness and thereby also breaking the first sealing connection means 3.

Further the seal mechanism may also be provided at the connection between the adsorption device 1 and the first external cap 9, and/or at the connection between the filter holder 2 and the second external cap 13, or is a modification of the third sealing connection means 14 and/or the fourth sealing connection means 19.

In the embodiment of the present invention where a second adsorption device and a second filter holder is attached, the seal mechanism is provided at the connection between the adsorption device 1 and the first external cap 9, at the connection between the adsorption device 1 and the filter holder 2, at the connection between the filter holder 2 and the second adsorption device, at the connection between the second adsorption device and the second filter holder, and/or at the connection between the second filter holder and the second external cap 23.

In the still further embodiment of the present invention where the sampling device does not have an adsorption device 1, a seal mechanism, with a view to preventing manipulation and tampering of the sampling device during transport and in connection with sampling and with a view to preventing use more than once of the sampling device, is provided at the connection between the filter holder 2 and the first external cap 9 and/or between the filter holder 2 and the second external cap 13.

The seal mechanism either may be chosen from a) a seal mechanism attached on the outer surface of the sampling device or b) is a modification of the first sealing connection means 3, wherein the first sealing connection means 3 will permanently lock the sampling device, the first sealing connection means 3 having a structural weakness with a view to enabling opening of the sampling device by breaking the structural weakness and thereby also breaking the first sealing connection means 3.

The sampling device according to the present invention can also be used for direct determination of the substance in question, in which case a color indicator, for instance, is brought into contact with the reacted substance in or adjacent to the sampling device.

The sampling device according to the present invention is particularly useful in laboratory and medical analysis methods.

While the invention has been described with reference to a number of embodiments, it will be understood by those skilled in the art that various changes may be made and equivalents may be substituted for elements thereof without departing from the scope of the present invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

The invention claimed is:

1. A fluid-tightly sealable sampling device for analysis of an at least one analyte in a sample of a fluid flowing through the sampling device, the sampling device having an inlet end and an outlet end and comprising:
    a hollow adsorption component having a lower edge surface, the hollow adsorption component containing or having immobilized thereto an at least one reagent for adsorption of and reaction with said at least one analyte in the sample of the fluid flowing through the sampling device;
    a hollow filter holder connected in a fluid-tight way with the hollow adsorption component, the hollow filter holder having an inner wall and an at least one receiving slot formed therein;
    a filter having a top surface, the filter containing or having immobilized thereto the at least one reagent for adsorption of and reaction with said at least one analyte in the sample of the fluid flowing through the sampling device;
    a gasket having a top surface, a bottom surface, a circumferential edge surface, and an at least one projection engaged with the at least one receiving slot in the hollow filter holder;
    a first external cap detachably connected with the inlet end of the sampling device in a fluid-tight way; and
    a second external cap detachably connected with the outlet end of the sampling device in a fluid-tight way;
    wherein the bottom surface of the gasket abuts the top surface of the filter, and the top surface of the gasket abuts the lower edge surface of the hollow adsorption component; and
    wherein the hollow adsorption component is locked to the hollow filter holder with a first sealing connection such that only forces in an axial direction in relation to a cross-section of the hollow adsorption component and the hollow filter holder are exerted by the gasket on the filter during assembling and handling of the sampling device.

2. The sampling device according to claim 1,
    wherein the first sealing connection comprises a receiving part located on the hollow adsorption component and a locking part located on the hollow filter holder; and
    wherein the first sealing connection is selected from the group consisting of a bayonet connection, a snap connection, and a thread connection.

3. The sampling device according to claim 1, wherein the first sealing connection is a sealing connection assembly comprising:
a first locking element adapted to at least partly enclose said hollow adsorption component and comprising an at least one gripping element,
a second locking element adapted to at least partly enclose said hollow filter holder,
wherein said at least one gripping element of said first locking element is adapted to sealingly engage said second locking element thereby locking said hollow adsorption component and said hollow filter holder together, and
said sealing connection assembly further comprises a resilient washer disposed between said first locking element and said second locking element.

4. The sampling device according to claim 3, further comprising an at least one protrusion on an outer side of said hollow adsorption component, said at least one protrusion being adapted to be received in said at least one receiving slot of said hollow filter holder, thereby preventing rotational movement between said hollow adsorption component and said hollow filter holder.

5. The sampling device according to claim 3, further comprising a third locking element being adapted to at least partly enclose said hollow filter holder and adapted to be disposed between said resilient washer and said hollow filter holder.

6. The sampling device according to claim 3, wherein said first locking element is integral with said hollow adsorption component.

7. The sampling device according to claim 3, wherein said second locking element is integral with said hollow filter holder.

8. The sampling device according to claim 1, wherein the hollow adsorption component is provided with a frusto-conical flange, which is inserted in a frusto-conical receiving part of the hollow filter holder in a fluid-tight way.

9. The sampling device according to claim 1, wherein the circumferential edge surface of the gasket abuts the inner wall of the hollow filter holder in a fluid-tight way.

10. The sampling device according to claim 1, wherein the hollow adsorption component is elongated, an inner cross-section of each of the hollow adsorption component and the hollow filter holder is circular, the gasket is annular, and the filter is formed as a flat cylinder.

11. The sampling device according to claim 1, wherein the gasket has an inner diameter which is smaller than an outer diameter of the filter, and is a support ring.

12. The sampling device according to claim 1, wherein the gasket is provided with two outward projections located at the circumferential edge surface thereof.

13. The sampling device according to claim 1, further comprising a calibration nozzle connected to an inlet end of the hollow adsorption component in a fluid-tight way via a fourth sealing connection.

14. The sampling device according to claim 13,
wherein the first external cap is detachably connected with the calibration nozzle via a second sealing connection, and
wherein the second external cap is detachably connected with the hollow filter holder.

15. The sampling device according to claim 14, wherein each of the second sealing connection and the fourth sealing connection is selected from the group consisting of a bayonet connection, a snap connection, a thread connection, and a sealing connection assembly.

16. The sampling device according to claim 1,
wherein the first external cap is detachably connected to the hollow adsorption component via a first fastener device having a first end attached to the first external cap and a second end detachably connected with a first receiving feature located on an outer surface of the hollow adsorption component; and
wherein the second external cap is detachably connectable with the hollow filter holder via a second fastener device having a first end attached to the second external cap and a second end detachably connected with a second receiving feature located on the outer surface of the hollow filter holder.

17. The sampling device according to claim 16,
wherein the first fastener device and the second fastener device are each selected from the group consisting of a string, a rope, a chain, a wire, and a cord; and
wherein each of the first and second receiving features is a loop.

18. The sampling device according to claim 1, wherein each of the first external cap and the second external cap has dimensions so as to be connectable to each other when detached from the sampling device, whereby an inner surface of each of said first external cap and said second external cap, respectively, is fluid-tightly sealed from the surroundings wherein the first external cap and the second external cap are connected to each other.

19. The sampling device according to claim 18, wherein the first external cap and the second external cap are connected to each other by inserting an open end of one of the first and second external caps into an open end of the corresponding other of the first and second external caps.

20. The sampling device according to claim 1,
wherein the sampling device is made of a plastic; and
wherein the plastic is selected from the group consisting of an anti-static plastic and an electrically conducting plastic.

21. The sampling device according to claim 1, wherein the hollow filter holder is adapted to connect to a pump.

22. The sampling device according to claim 1, further comprising a filter support disposed within the hollow filter holder.

23. The sampling device according to claim 22, wherein the filter support comprises radially extending projections running from the inner wall of the hollow filter holder towards a center of an inner cross-section of the hollow filter holder and ending close to said center of the inner cross-section.

24. The sampling device according to claim 1, wherein the hollow adsorption component contains an at least one elongated parallel smaller adsorption tubes connectable with the fluid flowing through the sampling device.

25. The sampling device according to claim 24, wherein the at least one elongated parallel smaller adsorption tube is provided with the at least one reagent immobilized on a wall surfaces thereof.

26. The sampling device according to claim 1, wherein the hollow adsorption component is provided with the at least one reagent immobilized on an inner wall surface thereof.

27. The sampling device according to claim 1, further comprising a seal mechanism provided at a connection location between the hollow adsorption component and the hollow filter holder such that after an initial assembling of the sampling device, it is visually evident or detectable when the hollow adsorption component is separated from the hollow filter.

28. The sampling device according to claim 27, wherein the seal mechanism is attached to an outer surface of the sampling device.

29. The sampling device according to claim 28, wherein the seal mechanism further comprises a seal mechanism disposed at an at least one connection locations in the group consisting of a connection location between the hollow adsorption component and the first external cap and a connection location between the hollow filter holder and the second external cap.

30. The sampling device according to claim 27, further comprising:
the hollow adsorption component comprising a first hollow adsorption component;
the hollow filter holder comprising a first hollow filter holder;
the filter comprising a first filter;
the gasket comprising a first gasket; and
a second hollow adsorption component, a second hollow filter holder, a second filter, and a second gasket;
wherein an inlet end of the second hollow adsorption component is fluid-tightly connected with an outlet end of the first hollow filter holder, an inlet end of the second filter holder is fluid-tightly connected with an outlet end of the second hollow adsorption component, and an outlet end of the second hollow filter holder is detachably connected with the second external cap in a fluid-tight way;
wherein the second filter is disposed within the second hollow filter holder and is securable by the second gasket having an at least one projection; and
wherein the second hollow adsorption component and the second hollow filter holder contain or have immobilized thereto an at least one reagent different from the at least one reagent provided in the first hollow adsorption component and the first hollow filter holder.

31. The sampling device according to claim 30, wherein a seal mechanism is provided at an at least one connection location in the group consisting of a connection location between the first hollow adsorption component and the first external cap, a connection location between the first hollow adsorption component and the first hollow filter holder, a connection location between the first hollow filter holder and the second hollow adsorption component, a connection location between the second hollow adsorption component and the second hollow filter holder, and a connection location between the second hollow filter holder and the second external cap.

32. The sampling device according to claim 27, wherein the seal mechanism is a frangible member for locking the sampling device.

33. The sampling device according to claim 1, wherein the gasket is an O-ring.

34. The sampling device according to claim 1, wherein the sampling device is made of polypropylene.

35. The sampling device according to claim 1, wherein the hollow adsorption component is provided with the at least one reagent immobilized on beads or particles packed within the hollow adsorption component.

36. The sampling device according to claim 1, wherein the hollow adsorption component is provided with the at least one reagent immobilized on at least one elongated structure disposed within the hollow adsorption component.

37. The sampling device according to claim 1, wherein the filter has the at least one reagent immobilized thereto.

38. The sampling device according to claim 1,
wherein the first sealing connection comprises a receiving part located on the hollow filter holder and a locking part located on the hollow adsorption component; and
wherein the first sealing connection is selected from the group consisting of a bayonet connection, a snap connection, and a thread connection.

39. The sampling device according to claim 1,
wherein the first external cap is detachably connected to the hollow adsorption component via a first fastener device having a first end detachably connected with a first receiving feature located on the first external cap and a second end attached to an outer surface of the hollow adsorption component; and
wherein the second external cap is detachably connectable with the hollow filter holder via a second fastener device having a first end detachably connected with a second receiving feature located on the second external cap and a second end attached to an outer surface of the hollow filter holder.

* * * * *